(12) United States Patent
Lane et al.

(10) Patent No.: US 8,778,962 B2
(45) Date of Patent: Jul. 15, 2014

(54) TREATMENT OF SOLID TUMORS WITH RAPAMYCIN DERIVATIVES

(75) Inventors: Heidi Lane, Basel (CH); Terence O'Reilly, Basel (CH); Jeanette Marjorie Wood, Biel-Benken (CH)

(73) Assignee: Novartis Pharmaceuticals Corporation, East Hanover, NJ (US)

( * ) Notice: Subject to any disclaimer, the term of this patent is extended or adjusted under 35 U.S.C. 154(b) by 0 days.

(21) Appl. No.: 13/546,686

(22) Filed: Jul. 11, 2012

(65) Prior Publication Data

US 2012/0283285 A1 Nov. 8, 2012

Related U.S. Application Data

(63) Continuation of application No. 10/468,520, filed as application No. PCT/EP02/01714 on Feb. 18, 2002, now Pat. No. 8,410,131.

(30) Foreign Application Priority Data

Feb. 19, 2001 (GB) .................................. 0104072.4
Oct. 17, 2001 (GB) .................................. 0124957.2

(51) Int. Cl.
| | | |
|---|---|---|
| *A61K 31/436* | (2006.01) | |
| *A61K 31/475* | (2006.01) | |
| *A61P 35/00* | (2006.01) | |
| *A61K 31/4196* | (2006.01) | |
| *A61K 45/06* | (2006.01) | |
| *A61K 31/439* | (2006.01) | |
| *A61K 39/395* | (2006.01) | |

(52) U.S. Cl.
CPC ....... *A61K 31/39558* (2013.01); *A61K 31/4196* (2013.01); *A61K 45/06* (2013.01); *A61K 31/475* (2013.01); *A61K 31/436* (2013.01); *A61K 31/439* (2013.01); *A61K 39/3955* (2013.01)
USPC .......................................................... 514/291

(58) Field of Classification Search
CPC .. A61K 31/436; A61K 45/06; A61K 2300/00
See application file for complete search history.

(56) References Cited

U.S. PATENT DOCUMENTS

| | | | |
|---|---|---|---|
| 4,885,171 | A | 12/1989 | Surendra et al. |
| 5,066,493 | A | 11/1991 | Sehgal et al. |
| 5,194,447 | A | 3/1993 | Kao |
| 5,206,018 | A | 4/1993 | Sehgal et al. |
| 5,362,718 | A | 11/1994 | Skotnicki et al. |
| 5,922,730 | A | 7/1999 | Hu et al. |
| 5,985,890 | A | 11/1999 | Cottens et al. |
| 6,333,348 | B1 | 12/2001 | Vogel et al. |
| 6,569,463 | B2 | 5/2003 | Patel et al. |
| 6,617,333 | B2 | 9/2003 | Rabindran et al. |
| 6,641,811 | B1 | 11/2003 | Suthanthiran et al. |
| 2002/0022054 | A1 | 2/2002 | Sawada et al. |
| 2002/0098278 | A1 | 7/2002 | Bates et al. |
| 2003/0100886 | A1 | 5/2003 | Segal et al. |
| 2003/0100887 | A1 | 5/2003 | Scott et al. |

FOREIGN PATENT DOCUMENTS

| | | | |
|---|---|---|---|
| EP | 1074263 | | 2/2001 |
| WO | 9409010 | | 4/1994 |
| WO | WO 94/09010 | * | 4/1994 ........... C07D 498/18 |
| WO | 95166191 | | 6/1995 |
| WO | 9528406 | | 10/1995 |
| WO | 9641807 | | 12/1996 |
| WO | 9747317 | | 12/1997 |
| WO | 9809970 | | 3/1998 |
| WO | 9811908 | | 3/1998 |
| WO | 0149338 | | 7/2001 |
| WO | 0151049 | | 7/2001 |
| WO | 0187372 | | 11/2001 |
| WO | 0205791 | | 1/2002 |
| WO | 0213802 | | 2/2002 |
| WO | 0240000 | | 5/2002 |
| WO | 02080975 | | 10/2002 |
| WO | 02098416 | | 12/2002 |

OTHER PUBLICATIONS

Newton et al. "Clinical presentation, diagnosis, and pharmacotherapy of patients with primary brain tumors." Ann Pharmacother. Jul.-Aug. 1999, 33(7-8); 816-32, abstract only.*
Lien et al. Therapeutic anti-VEGF antibodies. Therapeutic Antibodies, Handbook of Experimental Pharmacology 181. Y. Chernajovsky et al. (eds). 2008; 131-150.
Wikipedia (http://en.wikipedia.org/wiki/Angiogenesis, accessed Nov. 24, 2008 p. 1-12.
Geoerger et al. "Antitumor Activity of the Rapamycin Analog CCI-779 in Human Primitive Neuroectodermal Tumor/Medulloblastoma Models as SingleAgent and in Combination Chemotherapy", Cancer Res 2001, 61( 4): 1527-1532.
Guba et al. "Rapamycin Inhibits Tumor Growth and Metastasis by Antiangiogenesis", Chirurgisches Forum Fuer Experimentelle und Klinische Forschung, 2001, 37-39.
Law et al. "Farnesyltransferase Inhibitor Induces Rapid Growth Arrest and Blocks p70s6k Activation by Multiple Stimuli", J Biol Chem 2000, 275(15): 10796-10801.
Peng et al. "Novel Pyrrolo-quinoline Derivatives as Potent Inhibitors for P13-Kinase Related Kinases", Bioorg Med Chem 2002, 10(1): 167-174.
Shi et al. "Rapamycin Enhances Apoptosis and Increases Sensivity to Cisplatin in Vitro", Cancer Res. 1995, 55(9): 1982-1988.
Zhong et al. "Modulation of Hypoxia-inducible Factor 1-alpha Expression by the Epidermal Growth Factor/Phosphatidylinositol 3-Kinase/PTEV/AKT/FRAP Pathway . . .", Cancer Res. 2000, 60(6): 1541-1545.
Fossa et al. "Survival of patients with advanced urothelial cancer treated with cisplatin-based chemotherapy" British Journal of Cancer 1996, 74: 1655-1659.
Renal Pelvis (medical dictionary definition Dec. 12, 1998, accessed via http://www.mondofacto.com/facts/dictionary?renal+pelvis on May 19, 2011).
Arecci et al. "Immunosuppresants FK506 and Rapamycin Function as Reversal Agents of the Multidrug Resistance Phenotype", Blood 1992, 80(6): 1528-1536.
Dayanir et al. "Identification of Tyrosine Residues in Vascular Endothelial Growth", J Biol Chem 2001, 276(21): 17686-17692.
Eng et al. "Activity of Rapamycin (AY-22,989) Against Transplanted Tumors", J Antiobotics 1984, XXXVII(10): 1231-1237.
Zhu et al. "Inhibition of tumor growth and metastasis by targeting tumor-associated angiogenesis with antagonists to the receptors of vascular endothelial growth factor", Investigational New Drugs 1999, 17: 195-212.
Houghton, Peter J., "Everolimus", Clin Cancer Res. 16(5) (2010) p. 1-7.

* cited by examiner

*Primary Examiner* — Kortney L Klinkel
(74) *Attorney, Agent, or Firm* — Ann R. Pokalsky; Dilworth & Barrese, LLP

(57) ABSTRACT

Rapamycin derivatives have interesting effects in the treatment of solid tumours, optionally in combination with a chemotherapeutic agent.

6 Claims, No Drawings

TREATMENT OF SOLID TUMORS WITH RAPAMYCIN DERIVATIVES

This application is a continuation of U.S. application Ser. No. 10/468,520, filed Jan. 27, 2004, which is a 371 application of PCT/EP2002/01714, filed Feb. 18, 2002, which in its entirety is herein incorporated by reference.

The present invention relates to a new use, in particular a new use for a compound group comprising rapamycin and derivatives thereof.

Rapamycin is a known macrolide antibiotic produced by *Streptomyces hygroscopicus*. Suitable derivatives of rapamycin include e.g. compounds of formula I

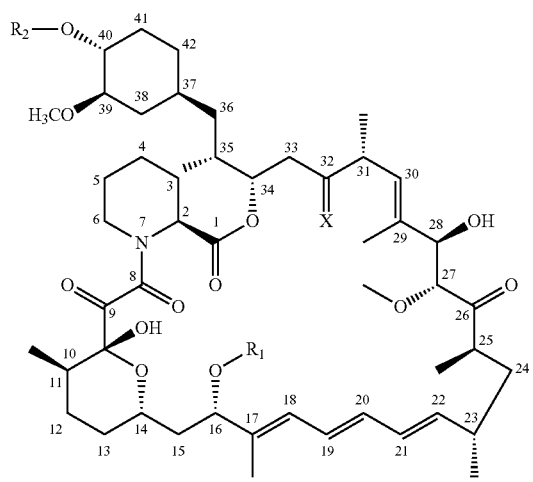

wherein
$R_1$ is $CH_3$ or $C_{3-6}$alkynyl,
$R_2$ is H or —$CH_2$—$CH_2$—OH, and
X is =O, (H,H) or (H,OH)
provided that $R_2$ is other than H when X is =O and $R_1$ is $CH_3$.

Compounds of formula I are disclosed e.g. in U.S. Pat. Nos: 5,665,772; 6,440,990; 5,985,890; and 6,200,985, which are incorporated herein by reference. They may be prepared as diclosed or by analogy to the procedures described in these references Preferred compounds are 32-deoxorapamycin, 16-pent-2-ynyloxy-32-deoxorapamycin, 16-pent-2-ynyloxy-32(S)-dihydro-rapamycin, 16-pent-2-ynyloxy-32(S)-dihydro-40-0-(2-hydroxyethyl)-rapamycin and, more preferably, 40-O-(2-hydroxyethyl)-rapamycin (referred thereafter as Compound A), disclosed as Example 8 in U.S. Pat. Nos: 5,665,772 and 6,440,990.

Compounds of formula I have, on the basis of observed activity, e.g. binding to macrophilin-12 (also known as FK-506 binding protein or FKBP-12), e.g. as described in WO 94/09010, WO 95/16691 or WO 96/41807, been found to be useful e.g. as immunosuppressant, e.g. in the treatment of acute allograft rejection. It has now been found that Compounds of formula I have potent antiproliferative properties which make them useful for cancer chemotherapy, particularly of solid tumors, especially of advanced solid tumors. There is still the need to expand the armamentarium of cancer treatment of solid tumors, especially in cases where treatment with anticancer compounds is not associated with disease regression or stabilization.

In accordance with the particular findings of the present invention, there is provided:

1.1 A method for treating solid tumors in a subject in need thereof, comprising administering to said subject a therapeutically effective amount of a compound of formula I.

1.2 A method for inhibiting growth of solid tumors in a subject in need thereof, comprising administering to said subject a therapeutically effective amount of a compound of formula I.

1.3 A method for inducing tumor regression, e.g. tumor mass reduction, in a subject in need thereof, comprising administering to said subject a therapeutically effective amount of a compound of formula I.

1.4 A method for treating solid tumor invasiveness or symptoms associated with such tumor growth in a subject in need thereof, comprising administering to said subject a therapeutically effective amount of a compound of formula I.

1.5 A method for preventing metastatic spread of tumours or for preventing or inhibiting growth of micrometastasis in a subject in need thereof, comprising administering to said subject a therapeutically effective amount of a compound of formula I.

By "solid tumors" are meant tumors and/or metastasis (whereever located) other than lymphatic cancer, e.g. brain and other central nervous system tumors (e.g. tumors of the meninges, brain, spinal cord, cranial nerves and other parts of central nervous system, e.g. glioblastomas or medulla blastomas); head and/or neck cancer; breast tumors; circulatory system tumors (e.g. heart, mediastinum and pleura, and other intrathoracic organs, vascular tumors and tumor-associated vascular tissue); excretory system tumors (e.g. kidney, renal pelvis, ureter, bladder, other and unspecified urinary organs); gastrointestinal tract tumors (e.g. oesophagus, stomach, small intestine, colon, colorectal, rectosigmoid junction, rectum, anus and anal canal), tumors involving the liver and intrahepatic bile ducts, gall bladder, other and unspecified parts of biliary tract, pancreas, other and digestive organs); head and neck; oral cavity (lip, tongue, gum, floor of mouth, palate, and other parts of mouth, parotid gland, and other parts of the salivary glands, tonsil, oropharynx, nasopharynx, pyriform sinus, hypopharynx, and other sites in the lip, oral cavity and pharynx); reproductive system tumors (e.g. vulva, vagina, Cervix uteri, Corpus uteri, uterus, ovary, and other sites associated with female genital organs, placenta, penis, prostate, testis, and other sites associated with male genital organs); respiratory tract tumors (e.g. nasal cavity and middle ear, accessory sinuses, larynx, trachea, bronchus and lung, e.g. small cell lung cancer or non-small cell lung cancer); skeletal system tumors (e.g. bone and articular cartilage of limbs, bone articular cartilage and other sites); skin tumors (e.g. malignant melanoma of the skin, non-melanoma skin cancer, basal cell carcinoma of skin, squamous cell carcinoma of skin, mesothelioma, Kaposi's sarcoma); and tumors involving other tissues including peripheral nerves and autonomic nervous system, connective and soft tissue, retroperitoneum and peritoneum, eye and adnexa, thyroid, adrenal gland and other endocrine glands and related structures, secondary and unspecified malignant neoplasm of lymph nodes, secondary malignant neoplasm of respiratory and digestive systems and secondary malignant neoplasm of other sites.

Where hereinbefore and subsequently a tumor, a tumor disease, a carcinoma or a cancer is mentioned, also metastasis in the original organ or tissue and/or in any other location are implied alternatively or in addition, whatever the location of the tumor and/or metastasis is.

In a series of further specific or alternative embodiments, the present invention also provides 1.6 A method for the treatment of a disease associated with deregulated angiogenesis in a subject in need thereof, comprising administering to said subject a therapeutically effective amount of rapamycin or a derivative thereof, e.g. CCI779, ABT578 or a compound of formula I.

1.7 A method for inhibiting or controlling deregulated angiogenesis in a subject in need thereof, comprising administering to said subject a therapeutically effective amount of rapamycin or a derivative thereof, e.g. CCI779, ABT578 or a compound of formula I.

1.8 A method for enhancing the activity of a chemotherapeutic agent or for overcoming resistance to a chemotherapeutic agent in a subject in need thereof, comprising administering to said subject a therapeutically effective amount of rapamycin or a derivative thereof, e.g. CCI779, ABT578 or a compound of formula I, either concomitantly or sequentially with said chemotherapeutic agent.

1.9 A method according to 1.8 wherein the chemotherapeutic agent is an inhibitor of signal transduction pathways directed either against host cells or processes involved in tumor formation and/or metastases formation or utilised by tumour cells for proliferation, survival, differentiation or development of drug resistance.

1.10 A method as indicated above, wherein rapamycin or a derivative thereof, e.g. CCI779, ABT578 or a compound of formula I is administered intermittently.

CCI779 is a rapamycin derivative, i.e. 40-[3-hydroxy-2-(hydroxymethyl)-2-methylpropanoate]-rapamycin or a pharmaceutically acceptable salt thereof, and is disclosed e.g. in U.S. Pat. No. 5,362,718. ABT578 is a 40-substituted rapamycin derivative further comprising a diene reduction.

Examples of diseases associated with deregulated angiogenesis include without limitation e.g. neoplastic diseases, e.g. solid tumors. Angiogenesis is regarded as a prerequisite for those tumors which grow beyond a certain diameter, e.g. about 1-2 mm.

In a series of further specific or alternative embodiments, the present invention also provides:

2.1 A compound of formula I for use in any method as defined under 1.1 to 1.5 above.

2.2 Rapamycin or a derivative thereof, e.g. CCI779, ABT578 or a compound of formula I for use in any method as defined under 1.6 to 1.10 above or 7 below.

3.1 A compound of formula I for use in the preparation of a pharmaceutical composition for use in any method as defined under 1.1 to 1.5 above.

3.2 Rapamycin or a derivative thereof, e.g. CCI779, ABT578 or a compound of formula I for use in the preparation of a pharmaceutical composition for use in any method as defined under 1.6 to 1.10 above or 7 below.

4.1 A pharmaceutical composition for use in any method as defined under 1.1 to 1.5 above comprising a compound of formula I together with one or more pharmaceutically acceptable diluents or carriers therefor.

4.2 A pharmaceutical composition for use in any method as defined under 1.6 to 1.10 above or 7 below comprising rapamycin or a derivative thereof, e.g. CCI779, ABT578 or a compound of formula I, e.g. Compound A, together with one or more pharmaceutically acceptable diluents or carriers therefor.

5.1 A pharmaceutical combination comprising a) a first agent which is rapamycin or a derivative thereof, e.g. CCI779, ABT578 or a compound of formula I, e.g. Compound A, and b) a co-agent which is a chemotherapeutic agent, e.g. as defined hereinafter.

5.2 A pharmaceutical combination comprising an amount of a) a first agent which is rapamycin or a derivative thereof, e.g. CCI779, ABT578 or a compound of formula I, e.g. Compound A, and b) a co-agent which is a chemotherapeutic agent selected from the compounds defined under paragraph (iv) or (v) below, to produce a synergistic therapeutic effect.

6. A method as defined above comprising co-administration, e.g. concomitantly or in sequence, of a therapeutically effective amount of rapamycin or a derivative thereof, e.g. CCI779, ABT578 or a compound of formula I, e.g. Compound A, and a second drug substance, said second drug substance being a chemotherapeutic agent, e.g. as indicated hereinafter.

7. A method for treating post-transplant lymphoproliferative disorders or a lymphatic cancer, e.g. for treating tumor invasiveness or symptoms associated with such tumor growth in a subject in need thereof, comprising co-administering to said subject, e.g. concomitantly or in sequence, of rapamycin or a derivative thereof, e.g. CCI779, ABT578 or a compound of formula I, e.g. Compound A, and a second drug substance, said second drug substance being a chemotherapeutic agent, e.g. as indicated hereinafter.

By "lymphatic cancer" are meant e.g. tumors of blood and lymphatic system (e.g. Hodgkin's disease, Non-Hodgkin's lymphoma, Burkitt's lymphoma, AIDS-related lymphomas, malignant immunoproliferative diseases, multiple myeloma and malignant plasma cell neoplasms, lymphoid leukemia, myeloid leukemia, acute or chronic lymphocytic leukemia, monocytic leukemia, other leukemias of specified cell type, leukemia of unspecified cell type, other and unspecified malignant neoplasms of lymphoid, haematopoietic and related tissues, for example diffuse large cell lymphoma, T-cell lymphoma or cutaneous T-cell lymphoma).

By the term "chemotherapeutic agent" is meant especially any chemotherapeutic agent other than rapamycin or a derivative thereof. It includes but is not limited to, i. an aromatase inhibitor,
ii. an antiestrogen, an anti-androgen (especially in the case of prostate cancer) or a gonadorelin agonist,
iii. a topoisomerase I inhibitor or a topoisomerase II inhibitor,
iv. a microtubule active agent, an alkylating agent, an antineoplastic antimetabolite or a platin compound,
v. a compound targeting/decreasing a protein or lipid kinase activity or a protein or lipid phosphatase activity, a further anti-angiogenic compound or a compound which induces cell differentiation processes,
vi. a bradykinin 1 receptor or an angiotensin II antagonist,
vii. a cyclooxygenase inhibitor, a bisphosphonate, a histone deacetylase inhibitor, a heparanase inhibitor (prevents heparan sulphate degradation), e.g. PI-88, a biological response modifier, preferably a lymphokine or interferons, e.g. interferon γ, an ubiquitination inhibitor, or an inhibitor which blocks anti-apoptotic pathways,
viii. an inhibitor of Ras oncogenic isoforms, e.g. H-Ras, K-Ras or N-Ras, or a farnesyl transferase inhibitor, e.g. L-744,832 or DK8G557,
ix. a telomerase inhibitor, e.g. telomestatin,
x. a protease inhibitor, a matrix metalloproteinase inhibitor, a methionine aminopeptidase inhibitor, e.g. bengamide or a derivative thereof, or a proteosome inhibitor, e.g. PS-341.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN™. Formestane can be administered, e.g., in the form as it is marketed, e.g. under the trademark LENTARON™. Fadrozole can be administered, e.g., in the form as it is marketed, e.g. under the trademark AFEMA™. Anastrozole can be administered, e.g., in the form as it is marketed, e.g. under the trademark ARIMIDEX™. Letrozole can be administered, e.g., in the form as it is marketed, e.g. under the trademark FEMARA™ or FEMAR™ Aminoglutethimide can be administered, e.g., in the form as it is marketed, e.g. under the trademark ORIMETEN™. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX™. Raloxifene hydrochloride can be administered, e.g., in the form as it is marketed, e.g. under the trademark EVISTA™. Fulvestrant can be formulated as disclosed in U.S. Pat. No. 4,659,516 or it can be administered, e.g., in the form as it is marketed, e.g. under the trademark FASLODEX™. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX™), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX™. Abarelix can be formulated, e.g. as disclosed in U.S. Pat. No. 5,843,901.

The term "topoisomerase I inhibitor" as used herein includes, but is not limited to topotecan, irinotecan, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR™. Topotecan can be administered, e.g., in the form as it is marketed, e.g. under the trademark HYCAMTIN™.

The term "topoisomerase II inhibitor" as used herein includes, but is not limited to the anthracyclines such as doxorubicin (including liposomal formulation, e.g. CAELYX™), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS™. Teniposide can be administered, e.g. in the form as it is marketed, e.g. under the trademark VM 26-BRISTOL™ Doxorubicin can be administered, e.g. in the form as it is marketed, e.g. under the trademark ADRIBLASTIN™. Epirubicin can be administered, e.g. in the form as it is marketed, e.g. under the trademark FARMORUBICIN™. Idarubicin can be administered, e.g. in the form as it is marketed, e.g. under the trademark ZAVEDOS™. Mitoxantrone can be administered, e.g. in the form as it is marketed, e.g. under the trademark NOVANTRON™.

The term "microtubule active agent" relates to microtubule stabilizing and microtubule destabilizing agents including, but not limited to taxanes, e.g. paclitaxel and docetaxel, vinca alkaloids, e.g., vinblastine, especially vinblastine sulfate, vincristine especially vincristine sulfate, and vinorelbine, discodermolides and epothilones and derivatives thereof, e.g. epothilone B or a derivative thereof. Paclitaxel may be administered e.g. in the form as it is marketed, e.g. TAXOL™. Docetaxel can be administered, e.g., in the form as it is marketed, e.g. under the trademark TAXOTERE™. Vinblastine sulfate can be administered, e.g., in the form as it is marketed, e.g. under the trademark VINBLASTIN R.P.™. Vincristine sulfate can be administered, e.g., in the form as it is marketed, e.g. under the trademark FARMISTIN™. Discodermolide can be obtained, e.g., as disclosed in U.S. Pat. No. 5,010,099.

The term "alkylating agent" as used herein includes, but is not limited to cyclophosphamide, ifosfamide, melphalan or nitrosourea (BCNU or Gliadel™). Cyclophosphamide can be administered, e.g., in the form as it is marketed, e.g. under the trademark CYCLOSTIN™. Ifosfamide can be administered, e.g., in the form as it is marketed, e.g. under the trademark HOLOXAN™.

The term "antineoplastic antimetabolite" includes, but is not limited to 5-fluorouracil, capecitabine, gemcitabine, methotrexate and edatrexate. Capecitabine can be administered, e.g., in the form as it is marketed, e.g. under the trademark XELODA™. Gemcitabine can be administered, e.g., in the form as it is marketed, e.g. under the trademark GEMZAR™.

The term "platin compound" as used herein includes, but is not limited to carboplatin, cis-platin and oxaliplatin. Carboplatin can be administered, e.g., in the form as it is marketed, e.g. under the trademark CARBOPLAT™. Oxaliplatin can be administered, e.g., in the form as it is marketed, e.g. under the trademark ELOXATIN™.

The term "compounds targeting/decreasing a protein or lipid kinase activity or further anti-angiogenic compounds" as used herein includes, but is not limited to protein tyrosine kinase and/or serine and/or threonine kinase inhibitors or lipid kinase inhibitors, e.g. compounds targeting, decreasing or inhibiting the activity of the epidermal growth factor family of receptor tyrosine kinases (EGFR, ErbB2, ErbB3, ErbB4 as homo- or heterodimers), the vascular endothelial growth factor family of receptor tyrosine kinases (VEGFR), the platelet-derived growth factor-receptors (PDGFR), the fibroblast growth factor-receptors (FGFR), the insulin-like growth factor receptor 1 (IGF-1R), the Trk receptor tyrosine kinase family, the Axl receptor tyrosine kinase family, the Ret receptor tyrosine kinase, the Kit/SCFR receptor tyrosine kinase, members of the c-Abl family and their gene-fusion products (e.g. BCR-Abl), members of the protein kinase C (PKC) and Raf family of serine/threonine kinases, members of the MEK, SRC, JAK, FAK, PDK or PI(3) kinase family, or of the PI(3)-kinase-related kinase family, and/or members of the cyclin-dependent kinase family (CDK) and anti-angiogenic compounds having another mechanism for their activity, e.g. unrelated to protein or lipid kinase inhibition.

Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58, 1998, 3209-3214, and by J. Mordenti et al in Toxicologic Pathology, Vol. 27, no. 1, pp 14-21, 1999; in WO 00/37502 and WO 94/10202; Angiostatin™, described by M. S. O'Reilly et al, Cell 79, 1994, 315-328; Endostatin™, described by M. S. O'Reilly et al, Cell 88, 1997, 277-285; anthranilic acid amides; ZD4190; ZD6474; SU5416; SU6668; or anti-VEGF antibodies or anti-VEGF receptor antibodies, e.g. RhuMab.

By antibody is meant intact monoclonal antibodies, polyclonal antibodies, multispecific antibodies formed from at least 2 intact antibodies, and antibodies fragments so long as they exhibit the desired biological activity.

Compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herpetin®), cetuximab, Iressa, OSI-774, CI-1033, EKB-569, GW-2016, E1.1, E2.4, E2.5, E6.2, E6.4, E2.11, E6.3 or E7.6.3.

Compounds which target, decrease or inhibit the activity of PDGFR are especially compounds which inhibit the PDGF receptor, e.g. a N-phenyl-2-pyrimidine-amine derivative, e.g. imatinib.

Compounds which target, decrease or inhibit the activity of c-Abl family members and their gene fusion products, e.g. a N-phenyl-2-pyrimidine-amine derivative, e.g. imatinib; PD180970; AG957; or NSC 680410.

Compounds which target, decrease or inhibit the activity of protein kinase C, Raf, MEK, SRC, JAK, FAK and PDK family members, or PI(3) kinase or PI(3) kinase-related family members, and/or members of the cyclin-dependent kinase family (CDK) are especially those staurosporine derivatives disclosed in EP 0 296 110, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; or LY333531/LY379196.

Further anti-angiogenic compounds are e.g. thalidomide (THALOMID) and TNP-470.

Compounds which target, decrease or inhibit the activity of a protein or lipid phosphatase are e.g. inhibitors of phosphatase 1, phosphatase 2A, PTEN or CDC25, e.g. okadaic acid or a derivative thereof.

Compounds which induce cell differentiation processes are e.g. retinoic acid, α-, γ- or δ-tocopherol or α-, γ- or δ-tocotrienol.

The term cyclooxygenase inhibitor as used herein includes, but is not limited to, e.g. celecoxib (Celebrex®), rofecoxib (Vioxx®), etoricoxib, valdecoxib or a 5-alkyl-2-arylaminophenylacetic acid, e.g. 5-methyl-2-(2'-chloro-6'-fluoroanilino)phenyl acetic acid.

The term "histone deacetylase inhibitor" as used herein includes, but is not limited to MS-27-275, SAHA, pyroxamide, FR-901228 or valproic acid.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL™. "Clodronic acid" can be administered, e.g., in the form as it is marketed, e.g. under the trademark BONEFOS™. "Tiludronic acid" can be administered, e.g., in the form as it is marketed, e.g. under the trademark SKELID™. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX™. "Ibandronic acid" can be administered, e.g., in the form as it is marketed, e.g. under the trademark BONDRANAT™. "Risedronic acid" can be administered, e.g., in the form as it is marketed, e.g. under the trademark ACTONEL™. "Zoledronic acid" can be administered, e.g. in the form as it is marketed, e.g. under the trademark ZOMETA™

The term "matrix metalloproteinase inhibitor" as used herein includes, but is not limited to collagen peptidomimetic and nonpetidomimetic inhibitors, tetracycline derivatives, e.g. hydroxamate peptidomimetic inhibitor batimastat and its orally bioavailable analogue marimastat, prinomastat, BMS-279251, BAY 12-9566, TAA211 or AAJ996.

In each case where citations of patent applications or scientific publications are given, the subject-matter relating to the compounds is hereby incorporated into the present application by reference. Comprised are likewise the pharmaceutically acceptable salts thereof, the corresponding racemates, diastereoisomers, enantiomers, tautomers as well as the corresponding crystal modifications of above disclosed compounds where present, e.g. solvates, hydrates and polymorphs, which are disclosed therein. The compounds used as active ingredients in the combinations of the invention can be prepared and administered as described in the cited documents, respectively. Also within the scope of this invention is the combination of more than two separate active ingredients as set forth above, i.e. a pharmaceutical combination within the scope of this invention could include three active ingredients or more. Further both the first agent and the co-agent are not the identical ingredient.

Utility of the compounds of formula I in treating solid tumors as hereinabove specified, may be demonstrated in animal test methods as well as in clinic, for example in accordance with the methods hereinafter described.

A. In Vitro

A.1 Antiproliferative Activity in Combination with Other Agents

A cell line, e.g. the compound A resistant A549 line ($IC_{50}$ in low nM range) versus the comparative Compound A resistant KB-31 and HCT116 lines ($IC_{50}$ in the μM range), is added to 96-well plates (1,500 cells/well in 100 μl medium) and incubated for 24 hr. Subsequently, a two-fold dilution series of each compound (Compound of formula I or a known chemotherapeutic agent) is made in separate tubes (starting at 8× the $IC_{50}$ of each compound) either alone or in paired combinations, and the dilutions are added to the wells. The cells are then re-incubated for 3 days. Methylene blue staining is performed on day 4 and the amount of bound dye (proportional to the number of surviving cells that bind the dye) determined. $IC_{50}$s are subsequently determined using the Calcusyn program, which provides a measure of the interaction, namely the so-called non-exclusive combination index (CI), where: CI ~1=the interaction is nearly additive; 0.85–0.9=slight synergism; <0.85=synergy. In this assay, the compounds of formula I show interesting antiproliferative activity in combination with another chemotherapeutic agent. For example the following CI values are obtained with a combination of Compound A and cisplatinum, paclitaxel, gemcitabine and doxorubicin, showing synergistic effects.

| Cell line | CI | | | |
|---|---|---|---|---|
| | Cisplatinum | Paclitaxel | Gemcitabine | Doxorubicin |
| KB-31 | 0.74 | 0.9 | 0.79 | 0.7 |
| A549 | 0.47 | 0.74 | 0.76 | 0.64 |
| HCT116 | 0.47 | 0.3 | 0.9 | 0.52 |

Furthermore, in this assay, Compound A potentiates the loss of A549 cell viability and cell death when it is used in combination with gemcitabine.

A.2 Antiangiogenic Activity

In vitro assay of the antiproliferative activity of rapamycin or a derivative thereof, e.g. Compound A, against human umbilical vein endothelial cells (HUVECs) demonstrates $IC_{50}$ values of $120\pm22$ pM and $841\pm396$, and >10 000 pM for VEGF- and bFGF- and FBS-stimulated proliferation, respectively. Additionally, no significant effects of Compound A on bFGF-stimulated normal human dermal fibroblast (NHDF) proliferation are observed over the same concentration range. These results indicate that Compound A inhibits the proliferation of HUVECs, being particularly potent against the VEGF-induced proliferation, VEGF being a key pro-angiogenic factor.

B. In Vivo

In the following assays, antitumor activity is expressed as T/C % (mean increase in tumor volumes of treated animals divided by the mean increase of tumor volumes of control animals multiplied by 100) and % regressions (tumor volume minus initial tumor volume divided by the initial tumor volume and multiplied by 100).

B.1 Activity in A549 Human Lung Tumor Xenografts

Fragments of A549 tumors (approx. 25 mg; derived from Cell line CCL 185, ATCC, Rockville Md., USA) are transplanted subcutaneously into the left flank of BALB/c nude mice. Treatment is started on day 7 or day 12 following tumor transplantation. The compound to be tested is administered p.o. once per day from day 7/12 to day 38/55, respectively. In this assay, when administered at a daily dose ranging from 0.1 mg/kg to 2.5 mg/kg, the compounds of formula I exhibit dose-dependent inhibition of tumor growth; for example in one representative experiment Compound A when administered at a dose of 2.5 mg/kg results in persisting regressions (41%); a dose of 0.5 mg/kg results in transient regressions (38% on day 17), with a final T/C of 16%, and a dose of 0.1 mg/kg slows tumor growth resulting in a final T/C of 43% (T/C for control animals is 100%).

B.2 Activity in KB-31 Human Epidermoid Tumor Xenografts

Fragments of KB-31 tumors (approx. 25 mg; derived from the cell lines obtained from Roswell Park Memorial Institute Buffalo, N.Y., USA) are transplanted subcutaneously into the left flank of BALB/c nude mice. Treatment is started on day 7 or on day 10 following tumor transplantation. The compound to be tested is administered p.o. once per day from day 7/10 to day 25/35, respectively. Antitumor activity is expressed as T/C % as indicated above. In this assay, when administered at a daily dose ranging from 0.5 mg/kg to 2.5 mg/kg, the compounds of formula I inhibit tumor growth; for example in one representative experiment Compound A when administered at a dose of 2.5 mg/kg/day results in a final T/C cvalue of 25% (T/C for control animals is 100%).

B.3 Activity in CA20948 Rat Pancreatic Tumors

Tumors are established in male Lewis rats by subcutaneous injection of CA20948 tumor cell suspension derived from donor rats into the left flank. Treatment is started on day 4 post inoculation. The compound to be tested is administered p.o. once per day (6 days a week) from day 4 to day 9-15 post inoculation. Antitumor activity is expressed as T/C % as indicated above. In this assay, when administered at a daily dose of 0.5 mg/kg to 2.5 mg/kg, the compounds of formula I inhibit tumor growth; for example in a representative experiment Compound A when administered p.o. at a daily dose of 2.5 mg/kg results in a final T/C value of 23%. In the same experiment, intermittent administration of Compound A, 5 mg/kg twice per week, results in a final T/C value of 32%. Compound A significantly and consistently decreases in these assays the rate of CA20948 pancreatic tumor growth when compared to vehicle controls (T/C for control animals is defined as 100%).

Compounds of formula I, e.g. Compound A, have been tested in further tumor models in accordance with the procedure as disclosed above. For example, a daily dosage of 2.5 mg/kg or 5 mg/kg Compound A produces final T/Cs of 18% and 9% when administered to the human NCI H-596 lung tumor model and the human MEXF 989 melanoma tumor model, respectively; 5 mg/kg produces final T/Cs of 20% (primary tumor) and 36% (cervical lymph node metastases) when administered to the orthotopic mouse B16/BL6 melanoma tumor model and 24% when administered to the human AR42J pancreatic tumor model; 2.5 mg/kg produces a final TIC of 28% when administered to the multi-drug resistant (MDR) human KB-8511 epidermoid tumor model. Good antitumor responses are also obtained when compounds of formula I, e.g. Compound A, are administered intermittently, e.g. 2 subsequent days per week or twice a week, to mice transplanted with human AR42J pancreatic tumors.

B.4 Combination with Doxorubicin

Mice transplanted with human KB-31 epidermoid tumors are treated for 21 days with doxorubicin at a dose of 5 mg/kg i.v. once per week, a compound of formula I, e.g. Compound A, at a dose of 2.5 mg/kg p.o once per day, or a combination of both. Thereafter compound of formula I treatment alone is continued in the combination group in order to determine if the compound of formula I can suppress the outgrowth of tumors that respond to conventional agents. Antitumor activity is expressed as T/C % or % regressions as indicated above. For example, the combination of Compound A and doxorubicin produces greater antitumor effect (74% regressions) as compared to either agent alone (Compound A, TIC 32%; doxorubicin 44% regressions). No exacerbation of the body weight losses caused by doxorubicin occurrs when Compound A treatment is added. Continuing Compound A treatment in the combination group, after ceasing doxorubicin, inhibits tumor outgrowth such that the tumor volumes of the doxorubicin monotherapy group are significantly larger than those of the combination group. Morever the combination appears to produce a greater cure rate (8/8 tumors) at 14 days post end of treatment than doxorubicin alone (3/8 tumors).

B.5 Combination with Cisplatinum

Mice transplanted with human NCI H-596 lung tumors are treated for 21 days with cisplatinum at a dose of 2.5 mg/kg i.v. once per week, a compound of formula I, e.g. Compound A, at a dose of 2.5 mg/kg p.o. once per day, or a combination of both. Antitumor activity is expressed as T/C % or % regressions as indicated above. A combination of Compound A and cisplatinum produces a greater antitumor effect (5% regressions) as compared to either agent alone (Compound A, TIC 26%; cisplatinum, TIC 26%). The combination did not lead to worsened tolerability.

B.6 Antiangiogenic Activity

B16/BL6 cells ($5\times10^4$) are injected intradermally into the ear of C57BU6 mice. Seven days later treatment with rapamycin or a derivative thereof e.g. Compound A, or vehicle is initiated. Primary tumor and cervical lymph nodes are collected after two weeks of daily treatment for measurement of vessel density. Endothelium of perfused vessels in the tumors is visualized using a nuclear staining dye (Hoechst 33342, 20 mg/kg) that is injected i.v. shortly before killing the mice. Tumors and metastases are snap frozen and sections examined under a light microscope equipped with an epifluorescent source. The fluorescence H33342-labelled endothelium cells is used to measure vessel number and size over the whole tumor section. Vessels are assigned to groups of 10 µm-size range. Distribution of vessel size is assessed using a histogram frequency analysis. At a dose of 5 mg/kg p.o., rapamycin or a derivative thereof reduces vessel density in both the primary tumor (e.g. T/C 50% for Compound A) and the metastases (e.g. T/C 40% for Compound A) as compared to controls. Rapamycin or a derivative thereof, e.g. Compound A, also changes vessel size distribution in the metastases.

B.7 Combination with an Antiangiogenic Agent

B16/BL6 cells ($5 \times 10^4$) are injected intradermally into the ear of C57BU6 mice. Seven days later treatment with rapamycin or a derivative thereof, e.g. Compound A, a VEGF receptor tyrosine kinase inhibitor, e.g. 1-(4-chloroanilino)-4-(4-pyridylmethyl)phthalazine or a salt thereof, e.g. the succinate, or a combination of both is initiated and effects on the growth and weight of the primary tumor and cervical lymph node metastases are monitored, respectively. Daily administration of the antiangiogenic agent (100 mg/kg p.o.) or of rapamycin or a derivative thereof, e.g. Compound A, (1 mg/kg p.o.) alone, reduces the size of the primary tumor (final T/C: 65% and 74%, respectively), whereas the combination of these two agents is synergistic (T/C 12%). Rapamycin or a derivative thereof, e.g. Compound A and the antiangiogenic agent treatment alone reduces cervical lymph node weights (related to regional metastases) (T/C: 75% and 34%, respectively), and the combination further reduces lymph node weights (T/C 13%). The treatments significantly promote body weight gains as compared to controls. For the primary tumors, analysis of possible interaction shows synergy with Compound A and antiangiogenic agent as antiangiogenic agent/controls=0.66; Compound A/controls=0.77; Compound A and antiangiogenic agent/controls=0.135. As Compound A and antiangiogenic agent/controls<Compound A/controls×antiangiogenic agent/controls (0.51), this is defined as synergy. For the metastases, analysis also shows synergy with Compound A and the antiangiogenic agent as antiangiogenic agent/controls=0.337; Compound A/controls=0.75; Compound A and antiangiogenic agent/controls=0.122. As Compound A and antiangiogenic agent/controls<Compound A/controls×antiangiogenic agent/controls (0.252), this is also defined as synergy (Clark, Breast Cancer Research Treatment 1997;46:255).

C. Clinical Trial

C.1 Investigation of Clinical Benefit of a Compound of Formula I, e.g. Compound A as Monotherapy in Solid Tumours Aim of the study: To identify the optimal dose of said compound, given orally once weekly, in a dose escalating study and the efficacy of the optimal dosage in solid tumours.

The study is divided into 2 parts:

Part 1:

Primary Aim: Identify the optimal dose of a compound of formula I, e.g. Compound A, given p.o. once weekly, assuming this should be the minimum dose associated with prolonged inhibition of mTOR and blood levels of said compound at least equivalent to those achieving an antitumor effect in in-vivo preclinical levels.

Secondary Aim: Assess safety of said compound when given alone to cancer patients and assess changes in tumor metabolic activity.

Design: Successive groups of 4 patients with advanced malignant solid tumors, refractory or resistant to standard therapies to receive a compound of formula I, e.g. Compound A, every 7 days different doses (group 1 to receive 5 mg; group 2 to receive 10 mg, group 3 to receive 20 mg) for 4 weeks. In week 4, establish the pharmacokinetic profile and the profile of mTOR inhibition as reflected by the inhibition of p70s6 kinase in peripheral lymphocytes. Carry out comparative 18-fluorodeoxyglucose (FDG) positron-emission tomography (FDG-PET) imaging (before $1^{st}$ dose, after $3^{rd}$ dose) to explore the change in tumor metabolism.

Patients main selection criteria: Adults with advanced-stage (III-V) solid tumors, resistant or refractory to standard therapies. At least one tumoral lesion should be measurable (>20 mm in one dimension).

Main variables for evaluation: Safety (adverse events), standard serum biochemistry and haematology, blood levels of the compound to be tested, lymphocyte p70-s6kinase activity, changes in tumor glucose uptake by FDG-PET.

Part 2:

Primary Aim: Explore the efficacy of a compound of formula I, e.g. Compound A, in patients with advanced solid tumors when given once a week at the optimal dosage, as identified in Part 1 as shown by tumor response.

Secondary Aim: Assess the safety of said compound at this dosage.

Design: 20 patients with progressing, advanced-stage solid tumors, resistant or refractory to standard therapies, to receive said compound at the dosage recommended as a result of Part 1. The general clinical state of the patient is investigated weekly by physical and laboratory examination. Changes in tumor burden are assessed every 2 months by radiological examination. Initially patients receive treatment for 2 months. Thereafter, they remain on treatment for as long as their disease does not progress and the drug is satisfactorily tolerated.

Main variables for evaluation: Safety (adverse events), standard serum biochemistry and haematology, tumor dimensions by computerised tomographic (CT) scan or magnetic resonance imaging (MRI).

C.2 Combined Treatment

Suitable clinical studies are, for example, open label non-randomized, dose escalation studies in patients with advanced solid tumors. Such studies prove in particular the synergism of the active ingredients of the combination of the invention. The beneficial effects on proliferative diseases can be determined directly through the results of these studies or by changes in the study design which are known as such to a person skilled in the art. Such studies are, in particular, suitable to compare the effects of a monotherapy using the active ingredients and a combination of the invention. Preferably, the dose of agent (a) is escalated until the Maximum Tolerated Dosage is reached, and the co-agent (b) is administered with a fixed dose. Alternatively, the agent (a) is administered in a fixed dose and the dose of co-agent (b) is escalated. Each patient receives doses of the agent (a) either daily or intermittent. The efficacy of the treatment can be determined in such studies, e.g., after 12, 18 or 24 weeks by radiologic evaluation of the tumors every 6 weeks.

Alternatively, a placebo-controlled, double blind study can be used in order to prove the benefits of the combination of the invention mentioned herein.

Daily dosages required in practicing the method of the present invention when a compound of formula I alone is used will vary depending upon, for example, the compound used, the host, the mode of administration and the severity of the condition to be treated. A preferred daily dosage range is about from 0.1 to 25 mg as a single dose or in divided doses. Suitable daily dosages for patients are on the order of from e.g. 0.1 to 25 mg p.o. Compound A may be administered by any conventional route, in particular enterally, e.g. orally, e.g. in the form of tablets, capsules, drink solutions, nasally, pulmonary (by inhalation) or parenterally, e.g. in the form of injectable solutions or suspensions. Suitable unit dosage forms for oral administration comprise from ca. 0.05 to 12.5 mg, usually 0.25 to 10 mg Compound A, together with one or more pharmaceutically acceptable diluents or carriers therefor.

The combination of the invention can also be applied in combination with surgical intervention, mild prolonged whole body hyperthermia and/or irradiation therapy.

The administration of a pharmaceutical combination of the invention results not only in a beneficial effect, e.g. a synergistic therapeutic effect, e.g. with regard to slowing down, arresting or reversing the neoplasm formation or a longer duration of tumor response, but also in further surprising beneficial effects, e.g. less side-effects, an improved quality of life or a decreased mortality and morbidity, compared to a monotherapy applying only one of the pharmaceutically active ingredients used in the combination of the invention, in particular in the treatment of a tumor that is refractory to other chemotherapeutics known as anti-cancer agents. In particular, an increased up-take of the co-agent (b) in tumor tissue and tumor cells is observed, when applied in combination with the first agent (a).

A further benefit is that lower doses of the active ingredients of the combination of the invention can be used, for example, that the dosages need not only often be smaller but are also applied less frequently, or can be used in order to diminish the incidence of side-effects, while controlling the growth of neoplasm formation. This is in accordance with the desires and requirements of the patients to be treated.

According to one embodiment of the invention, a preferred pharmaceutical combination comprises
a) a compound of formula I, e.g. Compound A, and
b) as co-agent, one or more compounds as indicated in paragraphs (ii), (iii) or (iv) above, e.g. carboplatin, cisplatinum, paclitaxel, docetaxel, gemcitabine or doxorubicin.

A synergistic combination of a compound of formula I, e.g. Compound A, with carboplatin, cisplatinum, paclitaxel, docetaxel, gemcitabine or doxorubicin is particularly preferred.

A further preferred pharmaceutical combination is e.g. a combination comprising
a) rapamycin or a derivative thereof, e.g. CCI-779, ABT578 or Compound A, and
b) as co-agent, one or more compounds as indicated under paragraphs (i) and (v) to (x) above, preferably one or more compounds as specified in paragraph (v) above.

Preferred is e.g. a synergistic combination of rapamycin or a derivative thereof, e.g. CCI-779, ABT578 or Compound A, with a compound which target, decrease or inhibit the activity of VEGFR, EGFR family, PDGFR, c-ABl family members or protein kinase C, e.g. as disclosed above.

One specific embodiment of the invention relates to the use of a combination of the invention for the prevention, delay of progression or treatment of or for the preparation of a medicament for the prevention, delay of progression or treatment of breast cancer. Preferably, in such embodiment the combination comprises as co-agent b) an aromatase inhibitor, e.g. the aromatase inhibitor letrozole, an anti-estrogen, e.g. tamoxifen, a topoisomerase II inhibitor, e.g. doxorubicin, or a microtubule active agent, e.g. paclitaxel.

Another embodiment of the invention relates to the use of a combination of the invention for the prevention, delay of progression or treatment of or for the preparation of a medicament for the prevention, delay of progression or treatment of lung cancer. Preferably, in such embodiment the combination of the invention comprises as co-agent b) a platin compound, e.g. carboplatin, or a microtubule active agent, e.g. paclitaxel.

Another embodiment of the invention relates to the use of a combination of the invention for the prevention, delay of progression or treatment of or for the preparation of a medicament for the prevention, delay of progression or treatment of pancreatic cancer. Preferably, in such embodiment the combination of the invention comprises as co-agent b) an antineoplastic antimetabolite, e.g. gemcitabine.

Another embodiment of the invention relates to the use of a combination of the invention for the prevention, delay of progression or treatment of or for the preparation of a medicament for the prevention, delay of progression or treatment of glioblastomas. Preferably, in such embodiment the combination of the invention comprises as co-agent b) an alkylating agent, e.g. BCNU.

A further embodiment of the invention relates to the use of rapamycin or a derivative thereof in combination with a chemotherapeutic agent in the treatment of a lymphatic cancer, e.g. as disclosed above. The combination may additionally comprise as co-agent b) busulfan, cytarabine, 6-thioguanine, fludarabine, hydroxyurea, procarbazine, bleomycin or methotrexate. Topoisomerase II inhibitors e,g. daunorubicin or, particularly, compounds which target, decrease or inhibit the activity of PDGFR or of c-Abl family members and their gene fusion products, e.g. imatinib are preferred as co-agent (b).

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

It is one objective of this invention to provide a pharmaceutical composition comprising a quantity, which is jointly therapeutically effective against a proliferative malignant disease comprising a combination of the invention. In this composition, the first agent a) and co-agent (b) can be administered together, one after the other or separately in one combined unit dosage form or in two separate unit dosage forms. The unit dosage form may also be a fixed combination.

The pharmaceutical compositions for separate administration of the first agent a) and co-agent b) and for the administration in a fixed combination, i.e. a single galenical composition comprising at least two combination partners a) and b), according to the invention can be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

Suitable pharmaceutical compositions contain, for example, from about 0.1% to about 99.9%, preferably from about 1% to about 60%, of the active ingredient(s). Pharmaceutical preparations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In particular, a therapeutically effective amount of each of the combination partner of the combination of the invention may be administered simultaneously or sequentially and in any order, and the components may be administered separately or as a fixed combination. For example, the method of delay of progression or treatment of a proliferative malignant disease according to the invention may comprise (i) administration of the first agent a) in free or pharmaceutically acceptable salt form and (ii) administration of a co-agent b) in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the invention may be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention may vary depending on the particular compound or pharmaceutical composition employed, the mode of administration, the condition being treated, the severity of the condition being treated. Thus, the dosage regimen of the combination of the invention is selected in accordance with a variety of factors including the route of administration and the renal and hepatic function of the patient. A physician, clinician or veterinarian of ordinary skill can readily determine and prescribe the effective amount of the single active ingredients required to prevent, counter or arrest the progress of the condition. Optimal precision in achieving concentration of the active ingredients within the range that yields efficacy without toxicity requires a regimen based on the kinetics of the active ingredients' availability to target sites.

Daily dosages for the first agent a) will, of course, vary depending on a variety of factors, for example the compound chosen, the particular condition to be treated and the desired effect. In general, however, satisfactory results are achieved on administration of rapamycin or a derivative thereof at daily dosage rates of the order of ca. 0.1 to 25 mg as a single dose or in divided doses. Rapamycin or a derivative thereof, e.g. a compound of formula I, may be administered by any conventional route, in particular enterally, e.g. orally, e.g. in the form of tablets, capsules, drink solutions or parenterally, e.g. in the form of injectable solutions or suspensions. Suitable unit dosage forms for oral administration comprise from ca. 0.05 to 10 mg active ingredient, e.g. Compound A, together with one or more pharmaceutically acceptable diluents or carriers therefor.

Fadrozole may be administered orally to a human in a dosage range varying from about 0.5 to about 10 mg/day, preferably from about 1 to about 2.5 mg/day. Exemestane may be administered orally to a human in a dosage range varying from about 5 to about 200 mg/day, preferably from about 10 to about 25 mg/day, or parenterally from about 50 to 500 mg/day, preferably from about 100 to about 250 mg/day. If the drug shall be administered in a separate pharmaceutical composition, it can be administered in the form disclosed in GB 2,177,700. Formestane may be administered parenterally to a human in a dosage range varying from about 100 to 500 mg/day, preferably from about 250 to about 300 mg/day. Anastrozole may be administered orallly to a human in a dosage range varying from about 0.25 to 20 mg/day, preferably from about 0.5 to about 2.5 mg/day. Aminogluthemide may be administered to a human in a dosage range varying from about 200 to 500 mg/day.

Tamoxifen citrate may be administered to a human in a dosage range varying from about 10 to 40 mg/day.

Vinblastine may be administered to a human in a dosage range varying from about 1.5 to 10 mg/m$^2$day. Vincristine sulfate may be administered parenterally to a human in a dosage range varying from about 0.025 to 0.05 mg/kg body weight-week. Vinorelbine may be administered to a human in a dosage range varying from about 10 to 50 mg/m$^2$day.

Etoposide phosphate may be administered to a human in a dosage range varying from about 25 to 115 mg/m$^2$day, e.g. 56.8 or 113.6 mg/m$^2$day.

Teniposide may be administered to a human in a dosage range varying from about 75 to 150 mg about every two weeks. Doxorubicin may be administered to a human in a dosage range varying from about 10 to 100 mg/m$^2$day, e.g. 25 or 50 mg/m$^2$day. Epirubicin may be administered to a human in a dosage range varying from about 10 to 200 mg/m$^2$day. Idarubicin may be administered to a human in a dosage range varying from about 0.5 to 50 mg/m$^2$day. Mitoxantrone may be administered to a human in a dosage range varying from about 2.5 to 25 mg/m$^2$day.

Paclitaxel may be administered to a human in a dosage range varying from about 50 to 300 mg/m$^2$day. Docetaxel may be administered to a human in a dosage range varying from about 25 to 100 mg/m$^2$day.

Cyclophosphamide may be administered to a human in a dosage range varying from about 50 to 1500 mg/m$^2$day. Melphalan may be administered to a human in a dosage range varying from about 0.5 to 10 mg/m$^2$day.

5-Fluorouracil may be administered to a human in a dosage range varying from about 50 to 1000 mg/m$^2$day, e.g. 500 mg/m$^2$day. Capecitabine may be administered to a human in a dosage range varying from about 10 to 1000 mg/m$^2$day. Gemcitabine hydrochloride may be administered to a human in a dosage range varying from about 1000 mg/m$^2$/week. Methotrexate may be administered to a human in a dosage range varying from about 5 to 500 mg/m$^2$day.

Topotecan may be administered to a human in a dosage range varying from about 1 to 5 mg/m$^2$day. Irinotecan may be administered to a human in a dosage range varying from about 50 to 350 mg/m$^2$day.

Carboplatin may be administered to a human in a dosage range varying from about 200 to 400 mg/m$^2$ about every four weeks. Cisplatin may be administered to a human in a dosage range varying from about 25 to 75 mg/m$^2$ about every three weeks. Oxaliplatin may be administered to a human in a dosage range varying from about 50 to 85 mg/m$^2$ every two weeks.

Imatinib may be administered to a human in a dosage in the range of about 2.5 to 850 mg/day, more preferably 5 to 600 mg/day and most preferably 20 to 300 mg/day.

Alendronic acid may be administered to a human in a dosage range varying from about 5 to 10 mg/day. Clodronic acid may be administered to a human e.g. in a dosage range varying from about 750 to 1500 mg/day. Etridonic acid may be administered to a human in a dosage range varying from about 200 to 400 mg/day. Ibandronic acid may be administered to a human in a dosage range varying from about 1 to 4 mg every three to four weeks. Risedronic acid may be administered to a human in a dosage range varying from about 20 to 30 mg/day. Pamidronic acid may be administered to a human in a dosage range varying from about 15 to 90 mg every three to four weeks. Tiludronic acid may be administered to a human in a dosage range varying from about 200 to 400 mg/day.

Trastuzumab may be administered to a human in a dosage range varying from about 1 to 4 mg/m$^2$/week.

Bicalutamide may be administered to a human in a dosage range varying from about 25 to 50 mg/m$^2$day.

1-(4-chloroanilino)-4-(4-pyridylmethyl)phthalazine or salt thereof, e.g. succinate, may be administered to a human in a dosage range of about 50 to 1500, more preferably about 100 to 750, and most preferably 250 to 500, mg/day.

The invention claimed is:
1. A method for inhibiting growth of non-malignant solid tumors of the brain in a subject, said method consisting of administering to said subject a therapeutically effective amount of a compound of formula I

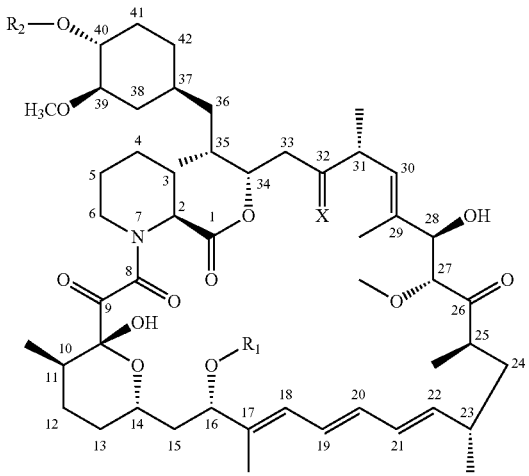

I wherein
R₁ is CH₃,
R₂ is —CH₂—CH₂—OH, and
X is =O.

2. The method of claim 1 wherein the compound of formula I is administered at a daily dose range of from about 0.1 to 25 mg, as a single dose or in divided doses.

3. The method of claim 1 wherein the compound of formula I is administered in a unit dosage form of from about 0.05 to 12.5 mg.

4. The method of claim 1 wherein the compound of formula I is administered in a unit dosage form of from about 0.25 to 10 mg.

5. The method of claim 1 wherein the compound of formula I is administered in a unit dosage form of 10 mg.

6. The method of claim 1 wherein the compound of formula I is administered orally.

* * * * *